United States Patent
Wondrak (12)

(10) Patent No.: US 6,319,720 B1
(45) Date of Patent: Nov. 20, 2001

(54) PROCESS FOR FAST VISUALIZATION OF PROTEIN

(76) Inventor: Ewald M. Wondrak, 411 Megan Ct., Frederick, MD (US) 21701

( * ) Notice: Subject to any disclaimer, the term of this patent is extended or adjusted under 35 U.S.C. 154(b) by 0 days.

(21) Appl. No.: 09/417,298

(22) Filed: Oct. 13, 1999

Related U.S. Application Data

(60) Provisional application No. 60/103,903, filed on Oct. 13, 1998, and provisional application No. 60/127,539, filed on Apr. 2, 1999.

(51) Int. Cl.$^7$ .................................................. G01N 33/48
(52) U.S. Cl. .............................. 436/86; 436/15; 436/164
(58) Field of Search ................................ 436/86, 15, 164

(56) References Cited

U.S. PATENT DOCUMENTS

| | | | |
|---|---|---|---|
| 4,023,933 | * 5/1977 | Bradford et al. | 436/87 |
| 4,219,337 | 8/1980 | Grossberg et al. | |
| 4,239,495 | * 12/1980 | Gindler et al. | 436/86 |
| 4,555,490 | 11/1985 | Merril | |
| 4,946,794 | 8/1990 | Berube | |
| 5,132,439 | * 7/1992 | Schultz et al. | 552/302 |
| 5,273,906 | 12/1993 | Shultz et al. | |
| 5,496,737 | * 3/1996 | Bickar | 436/86 |
| 5,705,649 | * 1/1998 | Shultz et al. | 548/125 |
| 5,922,186 | 7/1999 | Shukla et al. | |

OTHER PUBLICATIONS

Chu et al., "SDS–PAGE gel staining with GelCode blue stain reagent saves time and cost while delivering superior results", Previews (Jan.–Feb. 1998) 2(1):10–11.

"GelCode blue stain reagent eliminates the pain of having to destain", Previews (Jan.–Feb. 1998) 2(1):20.

Alger et al., "Rapid and ultrasensitive PAGE gel stains", Previews (Sep.–Oct. 1998) 2(3):14–16.

Meade–Tollin, "Rapid staining of gelatin zymograms with GelCode blue stain reagent", Previews (May–Jun. 1998) 2(2):2–4.

Kurien et al., "Heat mediated quick Coomassie blue protein staining and destaining of SDS–page gels", Indian J Biochem Biophys (Dec. 1998) 35:385–389.

Nivinskas et al., "Environmentally Benign Staining Procedure for Electrophoresis Gels Using Coomassie Blue", Bio Techniques (1996) 20:380–385.

"Colloidal Blue Stain Instructions", NOVEX product literature (Mar. 1999) 12 pp.

"Microwave Boosted Staining and Destaining", NOVEX internet website (Nov. 1999).

"GelCode Blue Stain Reagent", Pierce internet web site (Nov. 1999).

Chu et al., "Water wash–enhanced protein staining with GelCode coomassie blue stain reagent", Previews (Sep. 1997) 1(4):1–4.

\* cited by examiner

*Primary Examiner*—Jill Warden
*Assistant Examiner*—Monique T. Cole
(74) *Attorney, Agent, or Firm*—Pillsbury Winthrop LLP

(57) ABSTRACT

The present invention provides an improved method for staining proteins in and/or on a solid matrix or support. Typically, a protein-containing gel or membrane may be washed in a hot solution of water for about five minutes, stained in a hot solution of COOMASSIE brilliant blue dye in dilute aqueous mineral acid for about five minutes, and then rinsed in water. The washing and/or staining steps may be performed by placing the gel in a wash and/or staining solution, respectively, heating the solution in which the gel is placed to boiling in a microwave oven, and incubating the gel in the solution for about five minutes. The entire procedure can be performed in a little over ten minutes, which represents an enormous time savings over existing methods.

34 Claims, No Drawings

PROCESS FOR FAST VISUALIZATION OF PROTEIN

CROSS-REFERENCE TO RELATED APPLICATIONS

This application claims all benefits accruing under 35 U.S.C.119 (e) from the provisional applications U.S. application No. 60/103,903, filed Oct. 13, 1998, and U.S. application No. 60/127,539, filed Apr. 2, 1999. The contents of all U.S. patents, patent applications, and other publications are incorporated by reference herein.

BACKGROUND OF THE INVENTION

1. Field of the Invention

The present invention relates to the field of detection of proteins using synthetic dyes and, more particularly, to the detection of proteins in electrophoretic gels.

2. Description of the Related Art

One of the most commonly used and valuable methods for the separation and analysis of proteins is sodium dodecyl sulfate-polyacrylamide gel electrophoresis (SDS-PAGE). In this method, a sample containing protein is separated by electrophoresis in a sodium dodecyl sulfate-containing buffer through a polyacrylamide gel. As proteins are generally colorless, the gel is usually stained after electrophoresis to visualize the proteins.

A variety of methods are available for staining the proteins in such a gel. All of these methods, however, suffer from disadvantages that are addressed by the present invention.

For example, U.S. Pat. No. 4,555,490 (Merril) entitled "Rapid Visualization System for Gel Electrophoresis" describes a photodevelopment method involving silver ions. The procedure involves fixing the gel with methanol/acetic acid/citric acid solution, and using a methanolic silver nitrate solution. Methanol/acetic acid solutions have a considerable odor. This fixing solution is apparently essential prior to silver staining. Particular care must also generally be taken to avoid contact with silver nitrate solutions. Moreover, in addition to the contact and disposal problems associated with the use of silver ion, some care must apparently be taken to prevent silver salts from precipitating on the surface of the gel.

A number of methods use one of the dyes known as COOMASSIE brilliant blue to stain proteins. For example, U.S. Pat. No. 4,219,337 (Grossberg et al.) entitled "Assay for Proteins and Polypeptides" describes the use of COOMASSIE brilliant blue G250 in perchloric or hydrochloric acid, which couples with the protein and undergoes a color change. This patent does not describe the use of this reagent to stain proteins in polyacrylamide gels.

U.S. Pat. No. 4,946,794 (Berube) entitled "Visualization of Proteins on Electrophoresis Gels Using Planar Dyes" describes the use of COOMASSIE brilliant blue R250 or other dyes to stain proteins in polyacrylamide gels. The procedure requires a staining step in a methanol/acetic acid solution of the dye for one hour and a 15 minute potassium dichromate treatment to complex the dye and differentiate between the polyacrylamide matrix and the protein-containing spot. Thus, this procedure also requires the unpleasant use of methanol/acetic acid, and requires a one hour staining step.

U.S. Pat. No. 5,273,906 (Shultz et al.) entitled "Protein Staining Compositions and Methods" describes a series of derivatives of COOMASSIE dyes which are designed to overcome some of the problems usually associated with the use of COOMASSIE dyes in SDS-PAGE gels. However, in staining gels with these dyes, the staining solution is a methanolic solution, involving the problems associated with handling and disposal of methanol. Moreover, COOMASSIE brilliant blue dyes are more widely available and inexpensive than the derivatized COOMASSIE dyes of the Shultz patent.

In addition to the aforementioned patents, an article by Nivinskas et al. (BioTechniques 20:380–385, 1996) entitled "Environmentally Benign Staining Procedure for Electrophoresis Gels Using COOMASSIE Brilliant Blue" describes a procedure for staining gels with dilute aqueous solutions of COOMASSIE brilliant blue R. The SDS-PAGE gel was typically first rinsed and washed in a large volume of dilute HCl for two hours. The gel could be boiled in water, then rinsed, but this produced no difference in staining. The staining step involved overnight staining by a 0.0015% (w/v) solution of COOMASSIE brilliant blue G-250 in 1 mM HCl. Bands begin to appear after about one hour but the gel must be stained overnight (i.e., 16 hours) for maximal staining and quantitation, then destained with a large volume of 1 mM HCl and absorbent tissue wipes to absorb unbound dye. Although this method eliminates the problems associated with methanol and acetic acid, it is still slow and requires several solution changes.

Thus, I have noted that the existing methods of staining gels suffer either from problems of use of undesirable reagents, such as acetic acid and methanol or silver nitrate, or from long processing times. Additionally, I have noticed that some of the methods are inconsistent in the staining results, which can lead to the ruining of an experiment. Based on my reading of the contemporary art, I have determined that what is needed is a faster and easier way of staining proteins in and/or on solid matrices and supports.

SUMMARY OF THE INVENTION

It is therefore an object of my invention to provide an improved method of staining proteins embedded in and/or on a solid matrix (e.g., a gel or porous particle) or solid support (e.g., a membrane or porous filter).

It is also an object of the invention to provide a method of staining proteins which takes only a very short time (i.e., less than about one hour, 30 minutes, or 15 minutes).

It is a further object of the invention to provide a method of staining proteins which uses aqueous solutions.

It is a yet further object of the invention to avoid the use of certain noxious alcohols (e.g., methanol) and/or organic acids (e.g., acetic acid) as the solvent of the solutions being utilized, or a major component thereof.

It is a still further object of the invention to provide a staining method which consistently and reproducibly stains proteins.

It is a still further object of the invention to avoid the use of a special fixing step (e.g., acetic acid as a fixative) before protein staining.

These objects as well as other which will be apparent from the description below are achieved by the invention which provides a method for staining immobilized proteins (e.g., immobilized in a polyacrylamide slab gel, in an agarose or polyacrylamide bead, on and/or in a flexible membrane, on and/or in a disc or fiber filter) using at least one or two brilliant blue stains. This method may include the steps of: washing the immobilized protein(s) on and/or in a solid matrix or support in hot wash solution, staining the immobilized protein(s) in a hot staining solution containing brilliant blue dye in dilute acid, and rinsing the solid matrix or support to rinse the dye which is not associated with the immobilized protein(s). Washing and destaining steps may be considered as optional for performing the method of the invention, but they may improve the results obtained.

The wash solution may be water or a dilute acid (e.g., hydrochloric or perchloric acid). By "hot" is meant a solution heated to substantially above room temperature and the solution may cool thereafter or be maintained at the initial temperature. The hot wash solution may initially be at a temperature greater than 450° C., greater than 90° C., or brought to a boil. The washing step may be achieved by placing the gel in the wash solution and then removing the solution at the end of the incubation period. The wash solution may be heated in a microwave oven or on a hot plate, before or after the gel is placed therein, until the desired temperature is achieved.

Likewise, the staining solution is heated to substantially above room temperature; the hot staining solution may initially be at a temperature greater than about 45° C., greater than about 70° C., greater than about 90° C., or brought to a boil. The staining step may be achieved by placing the gel in the staining solution and then removing the solution at the end of the incubation period. The staining solution may be heated in a microwave oven or on a hot plate, before or after the gel is placed therein, until the desired temperature is achieved.

For a solid support (e.g., a membrane or filter), the entire procedure may be done at room temperature. Here, washing might not be required. But, as in the applications involving a solid matrix, extended rinsing (e.g., long incubation time, agitation, multiple changes of rinsing solution) may be used to destain the background staining initially present in and/or on the support or matrix after staining and thereby achieve increased sensitivity or reduction in the background. Thus, destaining may be useful but might not be required.

The brilliant blue dye may be used at a concentration in the range of about 0.0005 to 0.5% (w/v), preferably about 0.001 to 0.05% (w/v), in dilute acid. The dilute acid may be hydrochloric or perchloric acid; the concentration of dilute acid may be less than the equivalent of about 100 mM HCl, preferably in the range between about 5 and 50 mM HCl, and more preferably in the range between about 10 and 35 mM HCl. The staining solution may contain COOMASSIE brilliant blue G-250 at a final concentration of about 0.006% (w/v) in about 35 mM HCl or COOMASSIE brilliant blue R-250 at a final concentration of about 0005% (w/v) in about 10 mM HCl.

The solid matrix or support which has been stained in accordance with this method is also an object of the invention. In particular, such a product will not have been exposed to methanol and/or acetic acid during the process. The protein(s) immobilized on and/or in the product can be quickly processed for further analysis or storage. Preferred is a product in which staining of immobilized protein(s) is maximal and/or quantitative.

DETAILED DESCRIPTION OF THE INVENTION

The present invention is a staining procedure for proteins, especially those in and/or on gels, porous particles, membranes, and filters. The reagent for performing the procedure has been sold under the tradename SpeedStain as a kit for staining protein gels.

The present invention makes use of the dye compounds known as brilliant blue R and brilliant blue G, which are well known in the art and are available from a number of sources. They are also known by the tradenames COOMASSIE brilliant blue R and COOMASSIE brilliant blue G. These dyes are generally available as monosodium salts, although the nature of the counterion does not appear to be important. Brilliant blue G has Chemical Abstracts registry number [6104-58-1] and brilliant blue R has Chemical Abstracts registry number [6104-59-2]. Here, more success has been achieved with brilliant blue dye obtained from Bio-Rad Laboratories (Hercules, Calif.).

In the present patent application, the dyes brilliant blue R and brilliant blue G will be referred to as brilliant blue dyes. These dyes are available as powder or dissolved in ethanolic solutions and these solutions are often used to prepare methanolic staining solutions. Brilliant blue R has been used in strongly acidic solutions, such as 12.5% trichloroacetic acid, in which the dye is generally colloidal. Brilliant blue R is apparently even less soluble in acid than is brilliant blue G. In the present application, solutions of the brilliant blue dyes in dilute aqueous acids will be referred to as colloidal brilliant blue solutions. The colloidal and non-colloidal forms might be separated by filtration. Most or as much as 95% of the brilliant blue dye may be in the colloidal form when the staining solutions are prepared according to the present invention.

The present invention uses staining solutions of the brilliant blue dyes in a dilute acid solution with water or an aqueous buffer as the solvent. Preferably, the brilliant blue dye is dissolved in a dilute mineral acid solution. The acid used may be hydrochloric acid; alternatively, the acid used may be perchloric acid. It has been found, however, that phosphoric acid is not preferred. Alternatively, trichloroacetic acid (TCA) might also be used.

A typical brilliant blue G staining solution used in the present invention was made as follows: dissolve COOMASSIE brilliant blue G-250 in deionized water to achieve a final concentration of about 0.006% (w/v), stir the solution for about two hours at room temperature, and add concentrated hydrochloric acid to achieve a final concentration of about 35 mM HCl. Preferably, the dilute acid solution is equivalent to more than about 10 mM HCl and/or less than about 50 mM HCl.

A typical brilliant blue R staining solution used in the present invention was made as follows: dissolve COOMASSIE brilliant blue R-250 in deionized water to achieve a final concentration of about 0.0005% (w/v), stir the solution for about 24 hours at room temperature, and add concentrated hydrochloric acid to achieve a final concentration of about 10 mM HCl. Preferably, the dilute acid solution is equivalent to more than about 5 mM HCl and/or less than about 50 mM HCl.

The staining solutions used in the present invention may have a concentration of brilliant blue dye of between about 0.0005 and 0.5% (w/v); preferably, the concentration is between about 0.001 and 0.05% (w/v). A typical concentration of brilliant blue G is about 0.006% (w/v) and a typical concentration of brilliant blue R is about 0.0005% (w/v), but other concentrations may be used as well.

Hydrochloric acid or perchloric acid may be used as the dilute aqueous acid, and the dilute acid is preferably at a concentration in the range between about 1 and 50 mM. A preferred concentration of acid is between about 10 and 35 mM.

In the present application, the term "protein gel" refers to a gel in which proteins have been electrophoresed. The invention can also be used for gels in which the proteins have been separated by a method known as isoelectric focussing and for 2-D gels. The matrix may also be a porous particle. Additionally, the invention can be used to stain proteins on and/or in membranes or filters made from natural or artificial materials such as cellulose or derivatized versions thereof (e.g., nitrocellulose) and nylon or derivatized versions thereof (e.g., PVDF). The protein may also be applied to the solid matrix or support by capillary action or wicking, chromatography, electrophoresis or electrofocussing, or other methods such as, for example, western blotting and immunoblotting.

After electrophoresis is completed, the minigel was immersed in about 200 ml of deionized or distilled water or dilute acid, for example in a glass or plastic tray. The gel and the wash solution were placed in a microwave oven, heated until the solution boiled, and then washed for about five minutes. Alternatively, the tray containing the gel and wash solution may be placed on a hot plate and heated until the solution boils; heating may be stopped once the solution boils and the gel is allowed to incubate for about 5 minutes. Washing may remove materials which interfere with protein staining (e.g., SDS). The wash solution and the gel may be separated to remove the solution. The gel may be transferred from the wash solution to accomplish this, but generally the solution will be poured or aspirated away from the gel. Then, about 20 to 50 ml of a staining solution having a brilliant blue dye in dilute acid solution, was added to the gel.

The gel and the staining solution were placed in a microwave oven and heated until the solution boils. Typically, this took about 30 to 60 seconds but this may vary depending on the volume of solution and the power of the microwave oven. Alternatively, the tray containing the gel and brilliant blue solution may be placed on a hot plate and heated until the solution boils; heating may be stopped once the solution boils. The gel was incubated in the brilliant blue solution for about five minutes. The staining solution is preferably used only once because I have found that reuse results in a dramatic loss of sensitivity.

The brilliant blue solution was then removed from around the gel, and the gel was placed in deionized or distilled water for rinsing. The protein bands on the gel were now stained and visible to the eye as intense light blue bands (i.e., sky blue in the present invention in contrast to dark blue for conventional COOMASSIE staining). The gel is ready for photography, examination by eye, measurement of light transmission or adsorbance by an optical instrument, or other visualization methods. The gel may also be used for other further studies, such as drying or transfer to a solid support. If there is a sufficient amount of protein in the band, the rinsing solution merely washes the staining solution off the surface of the gel because no destaining (i.e., removal of brilliant blue dye trapped within the gel) is needed. But a light background in the gel may develop, and where a faint protein band is to be detected, this background may be removed by overnight washing.

Typically, in the present invention, protein bands containing as little as 20 ng are visible as intense blue bands against a light blue background. Optionally, after staining, the gel may be immersed in a solution of about 10 to 100 mM HCl acid which tends to fix the stained bands and remove the background of brilliant blue dye in the gel. This background is a very light blue throughout the gel due to the presence of some non-colloidal brilliant blue dye; this background can be reduced significantly by overnight washing. Isopropanol may intensify the color of the stained band while methanol and ethanol do not have this effect.

A solid matrix which has been stained may then have protein bands or spots immobilized in and/or on the matrix quantitated by an optical instrument using light transmission or adsorbance. The protein bands or spots may also be transferred to a solid support, stained, and quantitated by an optical instrument using light transmission or adsorbance. A laser densitometer can be used to scan the solid matrix or support and quantitate the amount of protein by comparison to a set of standard amounts. Staining is considered "maximal" when the amount of stain detected in a protein band or spot does not increase in a significant manner (i.e., staining is saturated). Because binding of brilliant blue dye by protein is stoichiometric, staining is considered "quantitative" when the amount of stain detected is directly related to the amount of protein present. Preferably, under the identical or similar conditions for performing the present invention, the set of standard amounts used to calibrate this quantitation can be plotted in a linear relationship to the amount of brilliant blue dye bound by protein in that region where the previously unknown amount of protein needs to be determined.

Alternatively, the washing and staining solutions may be used hot but below their boiling points. By "hot" is meant that the solution is heated to substantially above room temperature. For example, the hot wash solution may be at a temperature greater than about 45° C., greater than about 90° C., or brought to a boil. The washing step may be achieved by placing the gel in the wash solution and heating in a microwave oven or on a hot plate until the desired temperature is achieved. Alternatively, the solution may be preheated and poured over the gel or the gel may be transferred into the preheated solution.

Likewise, the hot staining solution is a solution heated to substantially above room temperature. For example, the hot staining solution may be at a temperature greater than about 45° C., greater than about 70° C., greater than about 90° C., or brought to boiling. The staining step may be achieved by placing the gel in the wash solution and heating in a microwave oven or on a hot plate until the desired temperature is achieved. Alternatively, the solution may be preheated and poured over the gel or the gel may be transferred into the preheated solution.

For staining proteins on a solid support, the entire staining procedure may be performed at room temperature. Hot solutions are not required when there is no solid matrix which needs to be penetrated.

The technique of PAGE is well known in the art. When electrophoresis of the polyacrylamide gel is completed, the gel is generally removed from the electrophoresis apparatus for staining. PAGE may be performed with gels of various sizes, polyacrylamide concentrations, and ratios of bis-acrylamide to acrylamide; with different electrophoretic buffer systems; in the presence or absence of sodium dodecyl sulfate (SDS). The present invention is here described for a protein minigel of polyacrylamide at a typical concentration between about 4 and 25% used for protein gels. Such SDS-PAGE gels has been maximally stained in about five minutes when the gel was about 1.0 mm thick, but increasing the thickness of the gel to about 1.5 mm results in a doubling of time to complete staining. The following example illustrates the invention but does not limit the legal protection of an issued patent unless a particular limitation is explicitly recited in the claims. For example, non-denaturing or non-polyacrylamide gels could be used in practicing the present invention under reducing and/or non-reducing conditions.

Bovine serum albumin (2 mg BSA per ml standard, Pierce) was diluted with phosphate buffered saline (PBS) to final concentrations of 1.0, 0.4, 0.2, 0.1, 0.04, 0.02, 0.01, 0.004 and 0.002 mg/ml. To 30 μl of these dilutions, 30 μl of a 2×SDS Tris-glycine sample Buffer (#LC2676, Novex) containing 10% (v/v) β-mercaptoethanol were added and incubated for three minutes in a boiling water bath. Ten μl of each sample were then loaded on a pre-cast 4–20% gradient polyacrylamide denaturing minigel (8×8 cm×1.0 mm; #EC60252, Novex) with 12-wells (4×9×1 mm in accordance with the comb that was used), and electrophoresed in an XCell II apparatus (#EI9001, Novex) using a 1:10 dilution of 10×Tris-glycine SDS running buffer (#LC2675, Novex) in deionized (d.i.) water at a constant voltage of 185 V for 60 minutes. Gels were removed from the apparatus and placed in 200 ml of d.i. water in a plastic tray (Nalgene).

The gel in water was placed in a microwave oven, heated for 3 minutes, and then incubated on a rocker for five minutes. The water was poured off from the gel. Then 40 ml of a staining solution having brilliant blue G-250 dye in 30 mM HCl, was added to the gel.

The gel and the staining solution were placed in a microwave oven and heated for one minute. The solution started boiling. The gel was incubated in the hot brilliant blue solution for five minutes with rocking. The brilliant blue solution was then removed from around the gel, and the gel was placed in d.i. water. The protein bands on the gel were now stained and visible to the eye and dilutions down to 20 ng of BSA were visible. This is similar to the sensitivity that can be achieved by conventional staining with a COOMASSIE dye.

The concentration of brilliant dye in the staining solution and/or incubation times may be increased by those skilled in the art if the amount or concentration of immobilized protein is decreased, a dimension of the solid matrix (e.g., thickness of a gel or diameter of a bead) is increased such that penetration by solution is decreased, or the like.

One advantage of the present invention is that the washing step performed before the staining step does not require acetic acid or methanol. One wash solution which may be used may be considered to consist essentially of water. Here, consist or consisting "essentially of" means that the solution is primarily water or simple aqueous solutions, without additives like acetic acid and alcohols which will increase the solubility of non-colloidal brilliant blue dye and therefore increase the background. This wash solution may be distilled or deionized water, but may also be tap water which has impurities which do not affect the washing. Alternatively, the wash solution may be a dilute perchloric or hydrochloric acid solution. Typically, a volume of wash solution greater than about ten times the volume of the gel is used once and then removed prior to staining the gel.

As described above, the entire procedure can be performed in as little as about ten minutes. The staining step of the procedure can be completed in as little as about five minutes, at which time bands will be visible and staining is maximal, for a 4–20% gradient polyacrylamide denaturing gel which is about 1.0 mm thick. Under these conditions and with destaining overnight, the sensitivity of the present invention is at least about 50 ng bovine serum albumin per $mm^3$ gel. In contrast, increasing the thickness of the gel to about 1.5 mm, doubles the time required for maximal staining but does not appreciably reduce sensitivity.

Therefore, the complete procedure takes considerably less time than the standard procedures, which usually involve a minimum staining time of about 20 minutes, and typically take more than an hour to as long as overnight to complete. By virtue of the short and simple procedure, there is no need to monitor the gel for the level of staining over a course of hours, which can be a great inconvenience.

Moreover, in the present procedure, there is no need to deal with the smell or disposal problems of methanol and acetic acid solutions. The dilute acids of the present invention may be neutralized to harmless solutions, and the dye may be adsorbed by charcoal, generally yielding a harmless aqueous solution for disposal. Furthermore, there is no appreciable shrinkage of the gel (i.e., much less than about 5%) using the present invention whereas there is on the order of 5–40% shrinkage of gels with acetic acid and methanol.

It is to be understood that the embodiments described herein are illustrative of the present invention, and that various modifications or changes in light thereof will be suggested to those of skill in the art, and are to be included within the scope of the appended claims. In this respect, the patent protection provided would be determined from the allowed claims and legal equivalents thereof instead of being limited by the specification.

I claim:

1. A method for staining a protein in a gel comprising staining the gel with a brilliant blue dye in a hydrochloric or perchloric acid solution, wherein said acid has a concentration equivalent of between 5 and 100 mM HCl, for an incubation time less than one hour and at an initial temperature of at least 45° C.

2. The method of claim 1, wherein said staining solution has an initial temperature of at least 70° C.

3. The method of claim 1, wherein said staining solution has an initial temperature of at least 90° C.

4. The method of claim 3, wherein said staining solution is heated in a microwave oven.

5. The method of claim 1, wherein said brilliant blue dye has a concentration in the staining solution from 0.0005% (w/v) to 0.5% (w/v).

6. The method of claim 1, wherein said brilliant blue dye is at least one of brilliant blue G and brilliant blue R.

7. The method of claim 1, further comprising washing the gel with a wash solution prior to staining the gel.

8. The method of claim 1, further comprising rinsing the gel to remove brilliant blue dye subsequent to staining the gel.

9. The method of claim 7, wherein said wash solution has an initial temperature of at least 45° C.

10. The method of claim 7, wherein said wash solution has an initial temperature of at least 70° C.

11. The method of claim 7, wherein said wash solution has an initial temperature of at least 90° C.

12. The method of claim 11, wherein said wash solution is heated in a microwave oven.

13. The method of claim 1, wherein the gel is not incubated in a solution containing acetic acid.

14. A method for staining a protein immobilized on a membrane comprising staining the membrane with a brilliant blue dye in a hydrochloric or perchloric acid solution, wherein said acid has a concentration less than 100 mM, for an incubation time less than 15 minutes.

15. A membrane, wherein protein bands or spots on the membrane are stained, prepared according to claim 14.

16. A method for staining a protein in a gel comprising:
(a) washing the gel with a wash solution prior to staining the gel;
(b) staining the gel with a staining solution for an incubation time less than 15 minutes and at an initial temperature of at least 70° C., wherein said staining solution contains colloidal brilliant blue dye in a dilute acid solution, said dilute acid has a concentration less than 100 mM, said brilliant blue dye has a concentration between 0.0005% (w/v) and 0.5% (w/v), and said brilliant blue dye is at least one of brilliant blue G and brilliant blue R; and (c) rinsing the gel to remove brilliant blue dye subsequent to staining the gel.

17. The method of claim 16, wherein said dilute acid has a concentration in the staining solution equivalent to between 5 mM and 50 mM HCl.

18. The method of claim 16, wherein said brilliant blue dye has a concentration in the staining solution from 0.001% (w/v) to 0.05% (w/v).

19. The method of claim 16, wherein said staining solution is heated in a microwave oven to maintain a temperature of at least 70° C.

20. A gel, wherein protein bands or spots in the gel are stained, prepared according to claim 16.

21. A method of staining protein comprising:

(a) providing protein immobilized in and/or on a solid matrix, and (b) staining said protein with a solution comprising at least one brilliant blue dye as colloids in a dilute acid solution;

wherein said dilute acid has a concentration equivalent of between about 1 mM and 100 mM, and said at least one brilliant blue dye has a concentration between 0.0005% (w/v) and 0.5% (w/v).

22. A membrane, wherein protein immobilized on said membrane is stained, prepared according to claim 21.

23. A gel, wherein protein immobilized in said gel is stained, prepared according to claim 21.

24. The method of claim 21, wherein said concentration of dilute acid is less than 50 mM.

25. The method of claim 21, wherein said concentration of dilute acid is less than 35 mM.

26. The method of claim 21, wherein said concentration of dilute acid is more than 5 mM.

27. The method of claim 21, wherein said concentration of dilute acid is more than 10 mM.

28. The method of claim 21, wherein said dilute acid has a concentration in the staining solution equivalent to between about 1 and 50 mM HCl.

29. The method of claim 25, wherein said dilute acid has a concentration in the staining solution equivalent to between about 10 and 35 mM HCl.

30. The method of claim 21, wherein said concentration of at least one brilliant blue dye is between about 0.001% (w/v) and 0.05% (w/v).

31. The method of claim 21, wherein said at least one brilliant blue dye is brilliant blue G-250 or brilliant blue R-250.

32. The method of claim 21, wherein the solution has a temperature of at least 45° C.

33. The method of claim 21, wherein the solution has a temperature of at least 70° C.

34. The method of claim 21, wherein the solution has a temperature of at least 90° C.

* * * * *